United States Patent [19]

Begrich

[11] Patent Number: 4,515,963
[45] Date of Patent: May 7, 1985

[54] PROCESS FOR PRODUCING 1,8-NAPHTHOLACTAM COMPOUNDS

[75] Inventor: Rainer Begrich, Rheinfelden, Switzerland

[73] Assignee: Ciba Geigy AG, Basel, Switzerland

[21] Appl. No.: 458,394

[22] Filed: Jan. 14, 1983

[30] Foreign Application Priority Data

Jan. 22, 1982 [CH] Switzerland ............................. 407/82

[51] Int. Cl.³ .......................................... C07D 487/00
[52] U.S. Cl. .................................................. 548/437
[58] Field of Search ........................................ 548/437

[56] References Cited

U.S. PATENT DOCUMENTS

| | | | |
|---|---|---|---|
| 3,347,865 | 10/1967 | Brack et al. | 548/437 |
| 4,246,410 | 1/1981 | Schwander et al. | 548/437 |
| 4,261,896 | 4/1981 | Tomcufcik et al. | 548/437 |

Primary Examiner—Robert Gerstl
Assistant Examiner—Cecilia Shen
Attorney, Agent, or Firm—Joseph G. Kolodny

[57] ABSTRACT

There is described a novel process for producing 1,8-naphtholactam compounds of the formula I

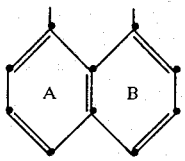 (I)

wherein the symbols R, A and B have the meanings defined in claim 1. This process comprises reacting a 1,8-naphtholactone compound of the formula II

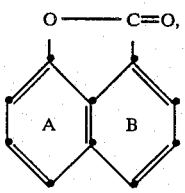 (II)

in an aqueous medium, with an amine of the formula III $$NH_2-R \quad (III),$$

optionally in the presence of bisulfite. The naphtholactam compounds of the formula I are obtained with a high degree of purity and with a yield of over 90%.

5 Claims, No Drawings

PROCESS FOR PRODUCING 1,8-NAPHTHOLACTAM COMPOUNDS

The invention relates to a novel process for producing 1,8-naphtholactam compounds of the formula I

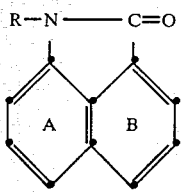

wherein R is hydrogen, an unsubstituted or substituted $C_1$–$C_4$-alkyl group, a cycloalkyl group or a substituted or unsubstituted aryl group, and the benzo rings A and/or B can be substituted. The novel process comprises reacting a 1,8-naphtholactone compound of the formula II

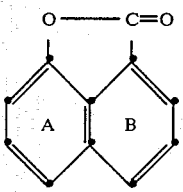

with an amine of the formula III

     (III), optionally in the presence of bisulfite.

When R is a $C_1$–$C_4$-alkyl group, this can be straight-chain or branched-chain. It is for example the methyl, ethyl, n-propyl or tert-butyl group. This $C_1$–$C_4$-alkyl group can be substituted; and substituents are for example: $C_1$–$C_4$-alkoxy groups, such as the methoxy, ethoxy, n-propoxy, n-butoxy or sec-butoxy group; halogen atoms, such as fluorine, chlorine or bromine; the OH group, the CN group, the COOH group, the CON(alkyl($C_1$–$C_4$))$_2$ group or the phenyl group. Where the substituent R is a cycloalkyl group, it is in particular the cyclohexyl group. When R is an aryl group, it is especially the phenyl group; this aryl group can be substituted for example by halogen (fluorine, chlorine or bromine), by $C_1$–$C_4$-alkyl (straight-chain and branched-chain), CN, $C_1$–$C_4$-alkoxy (straight-chain and branched-chain), by —COOH, CON(alkyl($C_1$–$C_4$))$_2$ or by $SO_2N$(alkyl($C_1$–$C_4$))$_2$.

If the benzo rings A and/or B are substituted, which can be the case once or several times, substituents are for example: halogen, such as fluorine, chlorine or bromine; cyano; $NO_2$; $C_1$–$C_4$-alkyl (straight-chain and branched-chain, such as methyl, ethyl, n-propyl or sec-butyl); $C_1$–$C_4$-alkoxy (straight-chain or branched-chain, such as methoxy, ethoxy or n-propoxy); $C_1$–$C_4$-alkylsulfonyl, such as methylsulfonyl or ethylsulfonyl; arylsulfonyl, such as phenylsulfonyl; acylamino, such as alkyl ($C_1$–$C_4$)-carbonylamino, for example acetylamino, and also benzoylamino; COOH; COO-alkyl ($C_1$–$C_4$); $CONH_2$; N-mono- and N,N-disubstituted (for example by $C_1$–$C_4$-alkyl) carboxylic acid amide; $SO_2NH_2$; or N-mono- and N,N-disubstituted (for example by $C_1$–$C_4$-alkyl)sulfonic acid amide, such as dibutylaminosulfonic acid amide.

The novel process is performed by reacting a 1,8-naphtholactone compound of the formula II, preferably in an aqueous medium, with an amine of the formula III, optionally in the presence of a bisulfite. It is possible either to suspend the compound of the formula II in water, and to then add the amine or the aqueous solution of the amine of the formula III; or to place the amine of the formula III or an aqueous solution thereof into the reaction vessel, and to subsequently add the compound of the formula II, if necessary as an aqueous suspension. It is however also possible to mix the compound of the formula II with the amine of the formula III, and to optionally then add water. Instead of being water, the reaction medium used can also be a lower aliphatic alcohol, for example methanol.

The reaction is advantageously performed in the presence of a bisulfite. Suitable bisulfites are for example alkali metal, ammonium and alkaline-earth metal bisulfites, such as in particular sodium bisulfite or calcium bisulfite. It is also possible however to add mixtures of various bisulfites to the reaction mixture, or the bisulfite salt of the amine of the formula III. The bisulfite is preferably added in the form of an aqueous solution (for example a 40% aqueous solution).

The reaction according to the present invention proceeds particularly well (relative to the yield of the naphtholactam compound of the formula I) when it is carried out with 2 to 10 equivalents, especially 2 to 5 equivalents, of the amine of the formula III, and in the presence of bisulfite. There are advantageously used 0.1 to 5 equivalents, in particular 0.5 to 2.5 equivalents, of the bisulfite, relative to the employed 1,8-naphtholactone of the formula II.

The reaction is preferably performed in an autoclave for about 1 to 24 hours at a temperature of about 100° to 200° C. At a temperature of 150° C., the reaction is finished after for example about 15 hours. The reaction mixture is subsequently allowed to cool, and the liquid phases are filtered off or separated. The 1,8-naphtholactam compounds of the formula I are thus obtained in a high degree of purity and with a yield of over 90%, relative to the employed lactone compound.

The naphtholactone compounds of the formula II are known, and can be produced by known methods. The following are for example used according to the invention:
naphtholactone-1,8,
4-chloronaphtholactone-1,8,
4-bromonaphtholactone-1,8,
2,4-dibromonaphtholactone-1,8,
5-cyanonaphtholactone-1,8,
4-methylsulfonyl-naphtholactone-1,8,
4-dibutylaminosulfonyl-naphtholactone-1,8,
5-ethyloxycarbonyl-naphtholactone-1,8, and
5-N-methyl-carbamoyl-naphtholactone-1,8.

The amines of the formula III are likewise known or are obtainable by known methods: the following for example can be used in the process according to the invention: ammonia, methylamine, ethylamine, n-propylamine, methoxyethylamine, 2-cyanoethylamine, 3-hydroxypropylamine, chloromethylamine, methanolamine, aniline, anisidine (o-, m-, p-), chloroaniline, toluidine, xylidine, aminobenzonitrile, aminobenzoic acid, dimethylanthranilamide and diethylsulfanilamide.

The 1,8-naphtholactam compounds of the formula I obtained by the process according to the invention can be used as intermediates in the synthesis of dyes, for example for producing by known processes acid dyes and disperse dyes, and also cationic dyes.

Compared with the known processes for producing the naphtholactam compounds of the formula I, the process according to the present invention is distinguished in particular by its efficiency in operation.

Compounds of the formula I wherein R is H are obtained by known processes, for example by reacting 1-naphthylamine with phosgene, and then closing the lactam ring with AlCl$_3$ according to the Friedel-Crafts method. The same compound is obtained also by reacting 1,8-naphthalenedicarboxylic acid anhydride with hydroxylamine, and subsequently with tosyl chloride to N-tosyloxy-1,8-naphthalenedicarbimide, and degrading this by degradation according to Lossen. Compounds of the formula I wherein R is not H are obtained by means of a multistage synthesis by way of the compound I wherein R is H and, for example, subsequent alkylation. The processes are often in all cases multistage processes.

The invention is further illustrated by the following Examples without being limited by them. Except where otherwise stated, 'parts' are parts by weight.

EXAMPLE 1

20 ml (about 5 equivalents) of aqueous ammonia are placed into an autoclave, and 8.5 g of 1,8-naphtholactone (in crystalline form) are slowly introduced. After several minutes' stirring, 20 ml (about 2 equivalents) of an NaHSO$_3$ solution (40% aqueous solution) are added, and stirring is subsequently maintained in the autoclave for 15 hours at 150° C. (pressure about 7.5 bar); the mixture is then diluted with 100 ml of water and filtered with suction. The residue is washed with about 200 ml of water and dried in vacuo. The yield is 7.7 g (=91%, relative to the employed 1,8-naphtholactone) of the naphtholactam compound of the formula

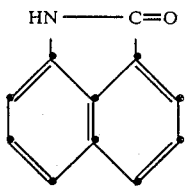

which has a melting point (crude) of 180° C.

EXAMPLE 2

4.1 parts of 3-methyl-N-methyl-benzomorpholine are dissolved in 12.5 parts of dichloroethane; there are then added successively 4.2 parts of 1,8-naphtholactam, obtained according to Example 1, 3 parts of phosphorus pentoxide and 10 parts of phosphorus oxychloride, and the mixture is heated to 80° C. It is condensed for 1 hour at 81°–83° C. and then cooled to 25° C.; 100 parts of water are slowly added dropwise and the pH is adjusted to about 9 with an aqueous solution of sodium hydroxide. Extraction is performed with 200 parts of ethyl acetate, and the solvent is distilled off. The yield is 7.5 parts of the dye of the formula

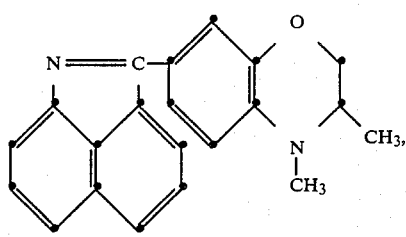

which, protonated for example with acetic acid, becomes soluble in water. There is obtained with this solution a reddish-blue dyeing on polyacrylonitrile fibres, which dyeing has very good general fastness properties.

EXAMPLE 3

The unsubstituted 1,8-naphtholactam can be obtained also by carrying out the reaction as described in Example 1 except for not adding bisulfite. The resulting product is, on the basis of thin-layer chromatographic results, identical to the 1,8-naphtholactam obtained according to Example 1.

EXAMPLE 4

1,8-Naphtholactam can be produced also in the following manner: 8.5 parts of 1,8-naphtholactone and 19.0 parts of sodium bisulfite are mixed together in 40 parts of methanol, and 25 parts of a saturated solution of ammonia in methanol are afterwards added. After 15 hours at 150° C. and under 14 bar in an autoclave, there is obtained in high yield 1,8-naphtholactam which, according to the thin-layer chromatogram and to the melting point, is identical to the product produced in Example 1.

EXAMPLES 5 to 22

By reacting in the respective cases the naphtholactone from column 1 of the following Table with the amine from column 2, the procedure otherwise being as described in Examples 1, 3 and 4, there is obtained in good yield and in high quality the specific naphtholactam listed in column 3, the melting point of which is given in column 4.

| 1 | 2 | 3 | 4 |
|---|---|---|---|
| 5 ![naphtholactone structure] | NH$_2$CH$_3$ | ![N-CH3 naphtholactam structure] | 74–76° C. |

-continued

| 1 | 2 | 3 | 4 |
|---|---|---|---|
| 6 | " | NH₂.CH₂.CH₃ | (naphthalimide with N—CH₂CH₃) | 69–70° C. |
| 7 | " | NH₂.CH₂CH₂CH₃ | (naphthalimide with NCH₂CH₂CH₃) | oil |
| 8 | " | NH₂.CH₂.CH₂.O.CH₃ | (naphthalimide with N—CH₂CH₂OCH₃) | 65–67° C. |
| 9 | " | H₂N.CH₂CH₂CN | (naphthalimide with N—CH₂CH₂CN) | 125–126° C. |
| 10 | " | H₂N—C₆H₄—NH₂ (aniline) | (naphthalimide with N-phenyl) | 99–102° C. |
| 11 | " | anthranilic acid (N₂N—C₆H₄—COOH) | (naphthalimide with N-(2-carboxyphenyl)) | 222–223° C. |

-continued
| | 1 | 2 | 3 | 4 |
|---|---|---|---|---|
| 12 | | NH₂.CH₃ | | 131–133° C. |
| 13 | " | NH₂.CH₂.CH₃ | | 152–154° C. |
| 14 | " | H₂N.CH₂CH₂CN | | 170° C. |
| 15 | | H₂N.CH₂CH₂CN | | 150° C. |
| 16 | | NH₃ | | 251–252° C. |
| 17 | " | H₂N.CH₃ | | 131–132° C. |
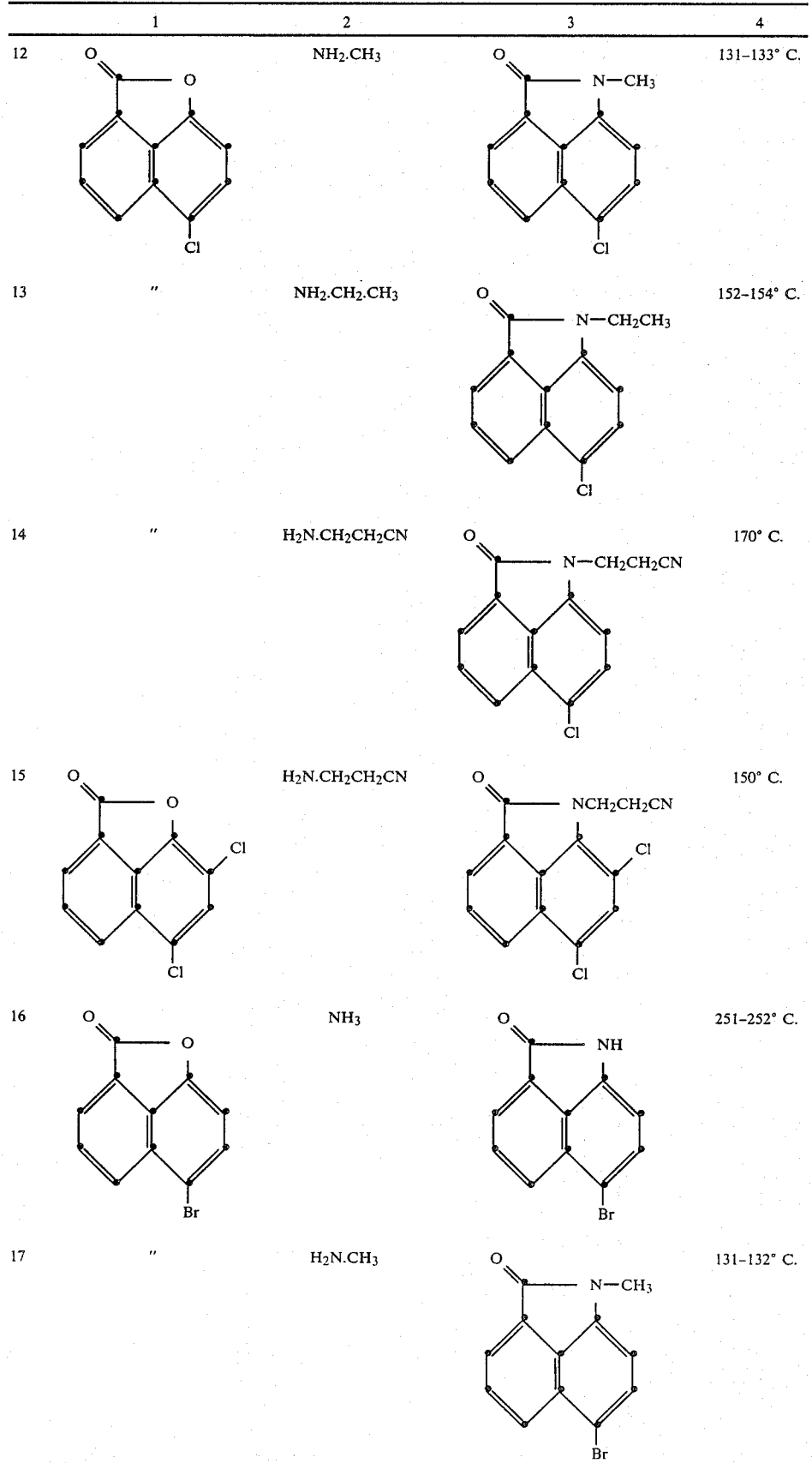

-continued

| | 1 | 2 | 3 | 4 |
|---|---|---|---|---|
| 18 | " | H₂N.CH₂CH₃ | 8-(N-ethyl)-5-bromo-1,8-naphtholactam | 103–107° C. |
| 19 | " | H₂N.CH₂CH₂CN | 8-(N-cyanoethyl)-5-bromo-1,8-naphtholactam | 200–205° C. |
| 20 | 5-cyano anhydride | H₂N.CH₃ | 8-(N-methyl)-5-cyano-1,8-naphtholactam | 204–209° C. |
| 21 | 5-ethoxycarbonyl anhydride | H₂N.CH₂CH₃ | 8-(N-ethyl)-5-ethoxycarbonyl-1,8-naphtholactam | 80–83° C. |
| 22 | 5-(N-methylcarbamoyl) anhydride | H₂N.CH₃ | 8-(N-methyl)-5-(N-methylcarbamoyl)-1,8-naphtholactam | 206–207° C. |

What is claimed is:

1. A process for producing a 1,8-naphtholactam compound of the formula I

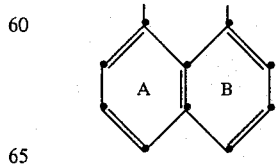

wherein R is hydrogen; a C₁–C₄-alkyl group optionally substituted by C₁–C₄-alkoxy, halogen, OH, CN, COOH, CON(alkyl $C_1$–$C_4$)$_2$ or phenyl; a cycloalkyl group or a phenyl group optionally substituted by halogen, $C_1$–$C_4$-alkyl, CN, $C_1$–$C_4$-alkoxy, COOH, CON(alkyl $C_1$–$C_4$)$_2$ or SO$_2$N-(alkyl $C_1$–$C_4$)$_2$, and the benzo rings A and/or B are unsubstituted or substituted once or several times by halogen, CN, NO$_2$, $C_1$–$C_4$-alkyl, $C_1$–$C_4$-alkoxy, $C_1$–$C_4$-phenylsulfonyl, arylsulfonyl, alkyl($C_1$–$C_4$)-carbamoylamino, benzoylamino, COOH, COO-alkyl($C_1$–$C_4$), CONH$_2$, CONH($C_1$–$C_4$-alkyl), CON($C_1$–$C_4$-alkyl)$_2$, SO$_2$NH$_2$, SO$_2$NH($C_1$–$C_4$-alkyl) or SO$_2$N($C_1$–$C_4$-alkyl)$_2$, which process comprises reacting a 1,8-naphtholactone compound of the formula II

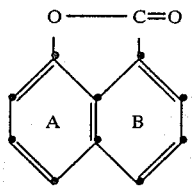
(II)

with an amine of the formula III

NH$_2$—R    (III), optionally in the presence of bisulfite.

2. A process according to claim 1, wherein the reaction is performed in an aqueous medium.

3. A process according to claim 1, wherein the reaction of the compound II with the amine of the formula III is performed in the presence of bisulfite.

4. A process according to claim 1, wherein there are used 2 to 10 equivalents of the amine of the formula III and 0.1 to 5 equivalents of the bisulfite compound, relative in each case to the 1,8-naphtholactone compound of the formula II.

5. A process according to claim 4, wherein there are used 2 to 5 equivalents of the amine of the formula III and 0.5 to 2.5 equivalents of the bisulfite compound, relative in each case to the 1,8-naphtholactone compound of the formula II.

* * * * *